United States Patent [19]

Chen et al.

[11] Patent Number: 5,728,402
[45] Date of Patent: Mar. 17, 1998

[54] CONTROLLED RELEASE FORMULATION OF CAPTOPRIL OR A PRODRUG OF CAPTOPRIL

[75] Inventors: Chih-Ming Chen; Jane Chang Chen, both of Cooper City; Jainbo Xie, Davie; Elliot Hahn, North Miami Beach, all of Fla.

[73] Assignee: Andrx Pharmaceuticals Inc., Fort Lauderdale, Fla.

[21] Appl. No.: 340,290

[22] Filed: Nov. 16, 1994

[51] Int. Cl.$^6$ .............................. A61K 9/22; A61K 9/28; A61K 9/52

[52] U.S. Cl. .................. 424/481; 424/457; 424/463; 424/468; 424/474; 424/475; 514/423

[58] Field of Search .......................... 424/463, 474, 424/481, 475, 457, 468; 514/423

[56] References Cited

U.S. PATENT DOCUMENTS

| | | |
|---|---|---|
| 3,065,143 | 11/1962 | Christenson et al. ............ 167/82 |
| 4,046,889 | 9/1977 | Ondetti et al. .................... 424/244 |
| 4,369,172 | 1/1983 | Schor et al. ....................... 424/19 |
| 4,389,393 | 6/1983 | Schor et al. ....................... 424/19 |
| 4,704,285 | 11/1987 | Alderman .......................... 424/468 |
| 4,756,911 | 7/1988 | Drost et al. ....................... 424/468 |
| 4,915,954 | 4/1990 | Ayer et al. ......................... 424/473 |

OTHER PUBLICATIONS

Metolose SR Brochure ShinEtsu, USP Hydroxypropyl Methylcellulose (1993).

Tech. Info. for Methoccel, Dow Chemical (1991).

*Primary Examiner*—Thurman K. Page
*Assistant Examiner*—James M. Spear
*Attorney, Agent, or Firm*—Hedman, Gibson & Costigan, P.C.

[57] ABSTRACT

The invention provides a controlled release pharmaceutical unit dose composition for oral administration which comprises: (a) an internal phase which comprises captopril or a prodrug of captopril in admixture with a hydrogel forming agent; and (b) an external phase which comprises a coating which resists dissolution in the stomach.

11 Claims, 4 Drawing Sheets

CONTROLLED RELEASE FORMULATION OF CAPTOPRIL OR A PRODRUG OF CAPTOPRIL

BACKGROUND OF THE INVENTION

The present invention relates to controlled release unit dose formulations of captopril. Captopril is widely employed as an agent which prevents the conversion of angiotensin I into angiotensin II by inhibition of angiotensin converting enzyme (ACE). This is the mechanism by which captopril acts as an antihypertensive agent. This drug is effective when orally administered.

After oral absorption of therapeutic doses of captopril in the form of the commercial product Capoten®, (includes microcrystalline cellulose, corn starch, lactose and magnesium stearate) in the absence of food, rapid absorption occurs with peak blood levels being observed at about one hour after oral administration. The presence of food in the gastrointestinal tract reduces absorption by 30 to 40%. The half life of captopril in the blood as measured by carbon-14 labeling shows that captopril has a half life of about 3 hours. It is believed that the actual half-life in the blood of unchanged captopril is actually less than two hours but this cannot be verified by existing techniques.

The usual dose for captopril is 25 mg to 100 mg administered orally two or three times a day. Because of the absorption problems caused by the interference of food in the gastrointestinal tract, directions for taking captopril advise the patient to take the drug one-hour before meals. In addition to the requirement for the administration of captopril one-hour before meals, the usual problem of patient compliance with a multidose regimen throughout the day has created a need for the preparation of an extended release oral dosage formulation of captopril that could be administered at extended intervals to avoid the absorption interference which is caused by food and to improve patient compliance. In addition the multi-dose therapy with captopril results in very high and very low levels of captopril being present depending on the timing of the administration of the drug. In addition, it would be desirable to provide a once a day formulation that would provide adequate therapeutic blood levels of captopril for about 24 hours.

Wilding et al., Pharmaceutical Research, Vol. 9, No. 5 p. 654 (1992) disclose that the commercially available tablet of captopril known as Capoten®, is poorly absorbed in the lower gastrointestinal tract.

Prodrugs of captopril have been described as being useful to enhance the absorption of captopril from the gastrointestinal tract. These drugs are converted in vivo into captopril after absorption. U.S. Pat. No. 5,073,641, which is incorporated by reference describes prodrugs of captopril.

SUMMARY OF THE INVENTION

The present invention provides a controlled release pharmaceutical unit dose composition for oral administration which comprises:
(a) an internal phase which comprises captopril or a prodrug of captopril in admixture with a hydrogel forming agent; and
(b) an external phase which comprises a coating which resists dissolution in the stomach.

The combination provides an effective controlled release formulation which provides extended blood levels of captopril with a decreased $C_{max}$ and permits the formulation of a once a day dosage form of captopril or a prodrug of captopril in order to provide a substantially continuous blood level of captopril or a prodrug of captopril throughout the day.

The discovery that the combination of a hydrogel and a coating which resists dissolution in the stomach can provide a once a day dosage unit is surprising and unexpected in view of the known short half life of captopril in the blood and the problems of lower gastrointestinal absorbance that are associated with captopril.

Accordingly it is a primary object of the invention to provide a controlled release oral unit dose formulation of captopril which will permit once a day administration to provide an extended therapeutic blood level of captopril for up to about 24 hours.

It is also an object of the invention to provide a novel prodrug of captopril which is described herein as the prodrug of Formula II.

These and other objects of the invention will become apparent from a review of the appended specification and drawings.

DETAILED DESCRIPTION OF THE INVENTION

The invention is concerned with a controlled release pharmaceutical unit dose composition for oral administration which is based on the combination of:
(a) an internal phase which comprises captopril or a prodrug of captopril in admixture with a hydrogel forming agent; and
(b) an external phase which comprises a coating which resists dissolution in the stomach.

Although the inventors do not wish to be bound by any theory which explains the operation of the invention, it is believed that the unit dosage form of the invention operates by the fact that the external phase substantially protects the internal phase from releasing any significant amount of the captopril in the stomach but gradually forms microscopic cracks when the unit dose reaches the duodenum. At that time the intestinal fluids pass through the cracks in the unit dose form and cause the hydrogel forming agent-captopril mixture to swell and diffuse through the cracks in the external phase of the unit dose form. The gradual release of the hydrogel forming agent-captopril mixture, as the unit dose is passed through the upper portion of the small intestine, results in the absorption of controlled, incremental amounts of the captopril which provide for prolonged therapeutic levels of the captopril in the blood and/or prevents the potentially toxic results which maybe caused by the high blood concentrations which result from the rapid absorption of captopril in the stomach.

Captopril is (S)-1-(3-mercapto-2-methyloxopropyl)-L-proline which is described in U.S. Pat. No. 4,046,889 which is incorporated by reference. The pro-drugs of captopril are also well known and many are described in U.S. Pat. Nos. 4,046,889 and 5,073,641, which are incorporated by reference.

The prodrugs of captopril include those of Formulas I, II, III and IV:

(I)

wherein R—COO— represents the acyloxy residue of captopril and $R_1$ and $R_2$ are the same or different and are selected from a group consisting of an alkyl group, an alkenyl group, an aryl group, an aralkyl group, a cycloalkyl group, in which the alkyl, alkenyl, aryl, aralkyl or cycloalkyl group is unsubstituted or substituted with one or more substituents selected from:

a halogen atom,
a hydroxy group,
a straight or branched-chain alkoxy group having the formula $R_3$—O—, wherein $R_3$ represents an alkyl group or any aryl group, which groups may be unsubstituted or substituted with one or more of a halogen atom or a hydroxy group,
a carbamoyl group having the formula wherein $R_4$ and $R_3$ are the same or different and are hydrogen, an alkyl group or are selected from a group having the formula —$CH_2NR_7R_6$ wherein $R_6$ and $R_7$ are the same or different and are hydrogen, or an alkyl group; an amino group having the formula —$NR_8R_9$, wherein $R_8$ and $R_9$ are the same or different and are hydrogen, or an alkyl group; an acyloxy group having the formula —$COOR_{10}$, wherein $R_{10}$ is an alkyl, aryl or aralkyl group; an oxyacyl group having the formula $R_{11}COO$— wherein $R_{11}COO$— wherein $R_{11}$ is hydrogen, an alkyl group, an aryl group, an aralkyl group, a cycloalkyl group, in which the alkyl, aryl, aralkyl or cycloalkyl group is unsubstituted or substituted with one or more of a halogen atom, a hydroxy group, an alkoxy group of the formula $R_3$—O— as defined above, a carbamoyl group of the formula —$CONR_4R_5$ as defined above or an amino group having the formula —$NR_8R_9$ as defined above; and nontoxic pharmaceutically acceptable acid addition salts thereof.

(II)

(III)

wherein $R_1$ is H or $R_3$ is a lower alkyl or phenyl $R_2$ is a lower alkyl or phenyl or and $R_4$, $R_5$ are H or a lower alkyl (IV)

wherein
$R_2$ is hydrogen or $R_5$—CO;
m is 2;
R is hydroxy, amino or lower alkoxy;
$R_1$ and $R_4$ each is hydrogen, lower alkyl or phenyl-lower alkyl;
$R_3$ is hydrogen, hydroxy or lower alkyl;
$R_5$ is lower alkyl, phenyl or phenyl-lower alkyl;
n is 0, 1 or 2 and basic salt thereof.

The invention includes the use of combinations of captopril and a prodrug of captoril in weight ratios of 5:95 to 95:5. A particular prodrug may be selected to achieve a particular blood level or duration of action in combination with the hydrogel and coating of the unit dosage form of the invention.

The preferred form of pharmaceutical unit dose of the invention is a tablet which has a compressed core comprising the drug and the hydrogel forming material which has a coating over the compressed core which comprises a sufficient amount of a coating which resists dissolution in the stomach. In the alternative, a hard or soft gelatin capsule may be filled with the captopril compound and the hydrogel forming material and the filled capsule may be provided with an appropriate coating which resists dissolution in the stomach.

The hydrogel forming materials include hydrophilic polymers which form hydrogels and have a molecular weight (number average) of 15,000 to 7,500,000 including hydrogel polysaccharides such as natural gums, seaweed extract, plant exudate, agar, agarose, algin, sodium alginate, potassium alginate, carrageenan, kappa-carrageenan, lambda-carrageenan, fucoidan, furcellaran, laminarin, hypnea, eucheuma, gum arabic, gum ghatti, gum karaya, gum tragacanth, guar gum, locust bean gum, quince, psyllium, flax seed, okra gum, arabinogalactin, pectin, xanthan, a swellable mixture of agar and carboxymethylcellulose mixed with a sparingly cross-linked agar, a blend of sodium alginate and locust bean gum, hydroxypropyl methylcellulose, hydroxy propyl cellulose and the like. These materials are described in U.S. Pat. Nos. 3,865,108; 4,002,173; 4,169,066; 4,207,893; 4,211,681; 4,271,143; 4,277,366; 4,327,725; 4,449,983; and 4,800,056 and in Handbook of Polymers, by Scott and Roff, Chemical Rubber Company, Cleveland, Ohio, all of which are incorporated by reference.

The coatings which may be used as the external phase of the unit dosage form of the invention include those which are described in Remington's Pharmaceutical Sciences, Mack Publishing Co., Easton, Pa., 1985 Ed., page 1637, which is incorporated by reference, as enteric coatings.

The preferred enteric coatings are shellac; cellulose acetate phthalate; hydroxypropyl methylcellulose phthalate; polyvinyl acetate phthalate; methacrylic acid ester copolymers; certain acrylic acid esters such as Eudragit S100;

L100; L30D which are manufactured by Röhm Pharma GmbH, or mixtures thereof. It is essential that a sufficient amount of the coating be applied to the internal phase of the unit dosage form of the invention which will prevent dissolution of the dosage form in the stomach. The amount to use may be determined by routine experimentation and will vary depending on the particular coating which is selected. In the case of shellac, it has been determined that the use of a total of 7–10 wt % based on the total weight of the tablet will provide good results. In the case of cellulose acetate phthalate, a test in dogs has determined that 7–10 wt % of the cellulose acetate phthalate based on the total weight of the tablet is insufficient to provide good results.

When the internal phase comprises a tablet core, it is preferred to add a pharmaceutically acceptable tablet lubricant to the core forming composition to facilitate the making of the tablet cores in high-speed automatic tabletting machines. These tablet lubricants comprise magnesium stearate, stearic acid, palmitic acid and like materials.

In most compositions, it will be desirable to add a pharmaceutical diluent to moderate the swelling effect of the hydrogel and/or to assist in the penetration of gastric fluid into the interior of the internal phase of the dosage form. These pharmaceutical diluents comprise, lactose, dextrose, sucrose maltose, fructose, galactose, microcrystalline cellulose, gelatin, polyvinylpyrrolidone, rice starch, corn starch, calcium carbonate and the like or mixtures thereof.

If desirable, an agent which is known as osmagent may be added to the hydrogel forming agent. An osmagent is a material which attracts fluid into the internal phase of the unit dosage formulation to assist in transporting the captopril to the exterior of the dosage form. These materials include electrolytes and organic acids. Example of useful materials include salts such as magnesium sulfate, sodium chloride, lithium chloride, potassium sulfate, sodium carbonate, sodium sulfate, lithium sulfate, potassium chloride, ammonium chloride, calcium sulfate, potassium acid phosphate, calcium lactate, mannitol, urea, inositol, magnesium succinate, tartaric acid, citric acid, itaconic acid, fumaric acid, lactic acid, ascorbic acid, malic acid, maleic acid and the like or mixtures thereof.

The unit dose compositions of the invention may comprise the following proportions of ingredients as the weight percent of all of the ingredients present in the formulation:

| 1. captopril or a pro-drug of captopril | 10–35 wt % |
| 2. hydrogel forming agent | 20–70 wt % |
| 3. external coating agent | 5–15 wt % |
| 4. pharmaceutical diluent | 0–50 wt % |
| 5. tablet lubricant | 0–2 wt % |
| 6. osmagent | 0–25 wt % |

Generally if a pharmaceutical diluent is employed it will be utilized at a level of from 15–35 wt %. The tablet lubricant, if present, will be present at a level of 1–2 wt % and the osmagent will be present at a level of 5–20 wt %.

Description of the Preferred Embodiments

EXAMPLE 1

Tablets were prepared by dissolving 1.58 g of the captopril prodrug of Formula II in 4.0 ml of ethanol which was combined with 2.1 g of hydroxypropyl methylcellulose (Methocel K100M; Number Av. Mol Wt 246,000; Nom. Visc. in 2% aq. soln.=100,000 cp.; 19–24 wt % methoxyl; 7–12 wt % hydroxylpropyl) which was moistened with 4.0 ml of water. Then, 2.15 g of lactose is blended into the mixture of the captopril prodrug and the hydroxypropyl methylcellulose, and the blended mixture is passed through a 20 mesh (US Standard sieve) prior to drying in an oven at about 50° C. Magnesium stearate (0.05 g) is then blended into the dried mixture and ten tablets weighing about 500 mg each are made by hand compression in a tablet mold.

The ten tablets are coated by hand dipping the tablets in a solution of 2.0 g of shellac in 10.0 g of ethanol until the tablets show a weight gain of about 7–10 wt % of the starting tablet weight.

The composition of the finished tablets was:

| captopril prodrug (Formula II) | 158 mg |
| hydroxypropyl methylcellulose | 195 mg |
| lactose | 200 mg |
| magnesium stearate | 10 mg |
| shellac | about 50 mg |

EXAMPLE 2

Using the procedure of Example I, tablets were made with the following composition:

| captopril | 100 mg |
| hydroxypropyl methylcellulose | 195 mg |
| lactose | 200 mg |
| magnesium stearate | 10 mg |
| shellac | about 50 mg |

(The hydroxypropyl methylcellulose is the same that was used in Example 1)

EXAMPLE 3

Fumaric acid (5.0 g) and sodium chloride (5.0 g) are pulverized in a mortar and pestle and 10.0 g of captopril; 20.0 g of hydroxypropyl methylcellulose; and 19.4 g of lactose are added, mixed and passed through a 30 mesh sieve prior to mixing with 0.6 g of magnesium stearate. Ten tablets were made and coated with shellac according to the procedure of Example 1. The finished tablets had the following composition:

| captopril | 100 mg |
| hydroxypropyl methyl cellulose | 200 mg |
| lactose | 194 mg |
| magnesium stearate | 6 mg |
| fumaric acid | 50 mg |
| sodium chloride | 50 mg |
| shellac | about 50 mg |

EXAMPLE 4

Using the general procedures of Examples 1 and 2 tablets were prepared which had 101 mg of the prodrug of Example 1 (equivalent to 68 mg of captopril) and 77 mg of captopril. Both of these batches of tablets were provided with a 10 wt % shellac coating according to the procedure of Example 1. A control tablet containing 70 mg of captopril was prepared which had no shellac coating and no hydrogel forming agent in the core.

COMPARATIVE EXPERIMENT

Tablets were prepared according to the general procedure of Example 1 which contained 72.8 mg of the prodrug of captopril and 49.02 mg of captopril but no shellac coating.

The coating was 7–10 wt %, based on the total tablet weight, of cellulose acetate phthalate. The tablets were administered at different times to a 7.5 kg fasting dog and the plasma concentrations were determined by high pressure liquid chromatography at 1, 2 3, 4, 6, 8, 10, and 12 hours and are shown on FIG. 4. It is believed that the short duration of activity was due to the use of an insufficient amount of coating material that was resistant to dissolution in the stomach.

EXAMPLE 5

The captopril prodrug of Formula II is prepared by reacting, under reflux conditions, a 10% molar excess of acetic anhydride with about 10 g of captopril which is dissolved in about 50 ml of chloroform. The reaction mixture is cooled and mixed with water which is acidified with 0.1N HCl. The thio acetyl derivative is isolated and is then dissolved in methylene chloride and is reacted with alphahydroxy dimethyl acetamide in the presence of N,N-dicyclohexylcarbodiimide. After the reaction is complete, the solution is mixed with water and a compound of formula II is obtained.

The tablets prepared in Examples 1, 2 and 3 were tested in fasting, healthy human male volunteers using 100 mg Capoten® tablets as a control. The Capoten' tablets did not contain any hydrogel in the core or any external coating that resisted dissolution in the stomach.

Blood samples were withdrawn at 0, 1, 3, 5, 7, 9, 12, 15 and 24 hours and the separated plasma was assayed for captopril using high pressure liquid chromatography.

Figure 1:
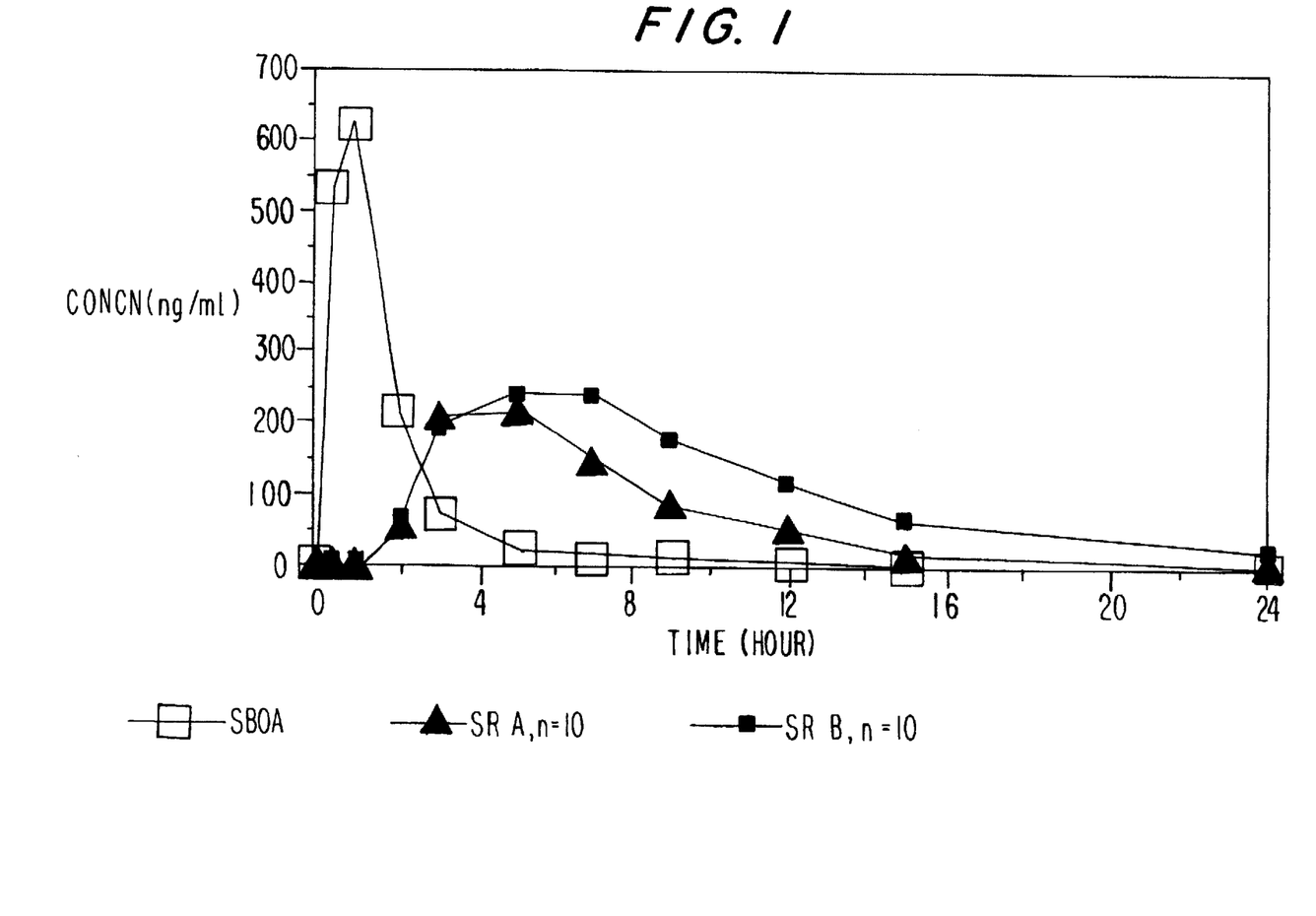
FIG. 1 is a graphical representation of the blood levels which were determined after oral administration to humans of formulations of the invention.

FIG. 1 shows the average of the results of the tests of the formulation of Example 1 (SRB); Example 2 (SRA) and the literature values for captopril (SBOA) (Capoten®). The data on FIG. 1 shows that the tablets prepared according to the invention provide blood levels of captopril which permit once a day administration while the prior art tablets of captopril produce measurable blood levels for only up to about 12 hours which does not permit once a day administration.

Figure 2:
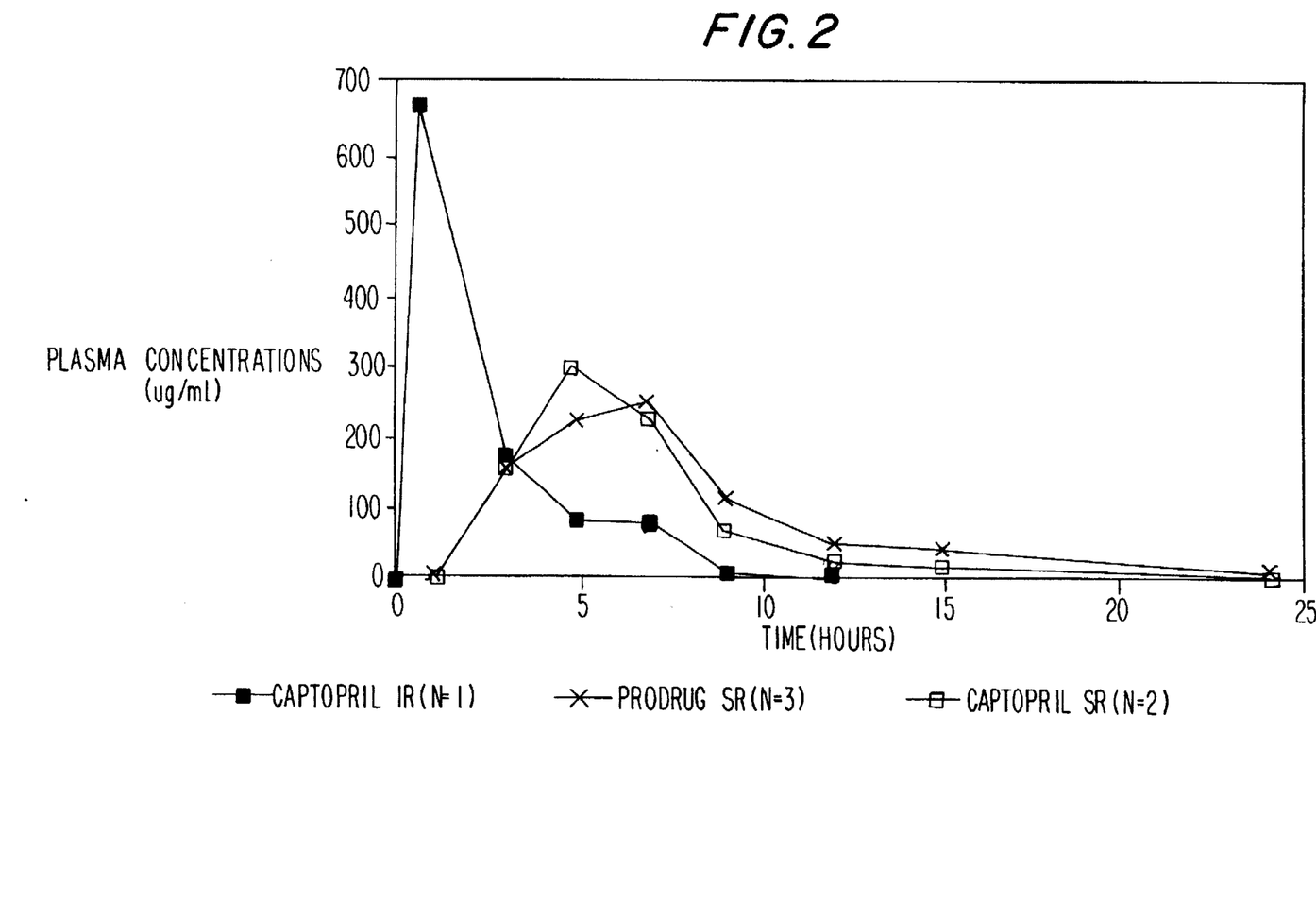
FIG. 2 is a graphical representation of the blood levels which were determined after oral administration to humans of formulations of the invention.
Figure 3:
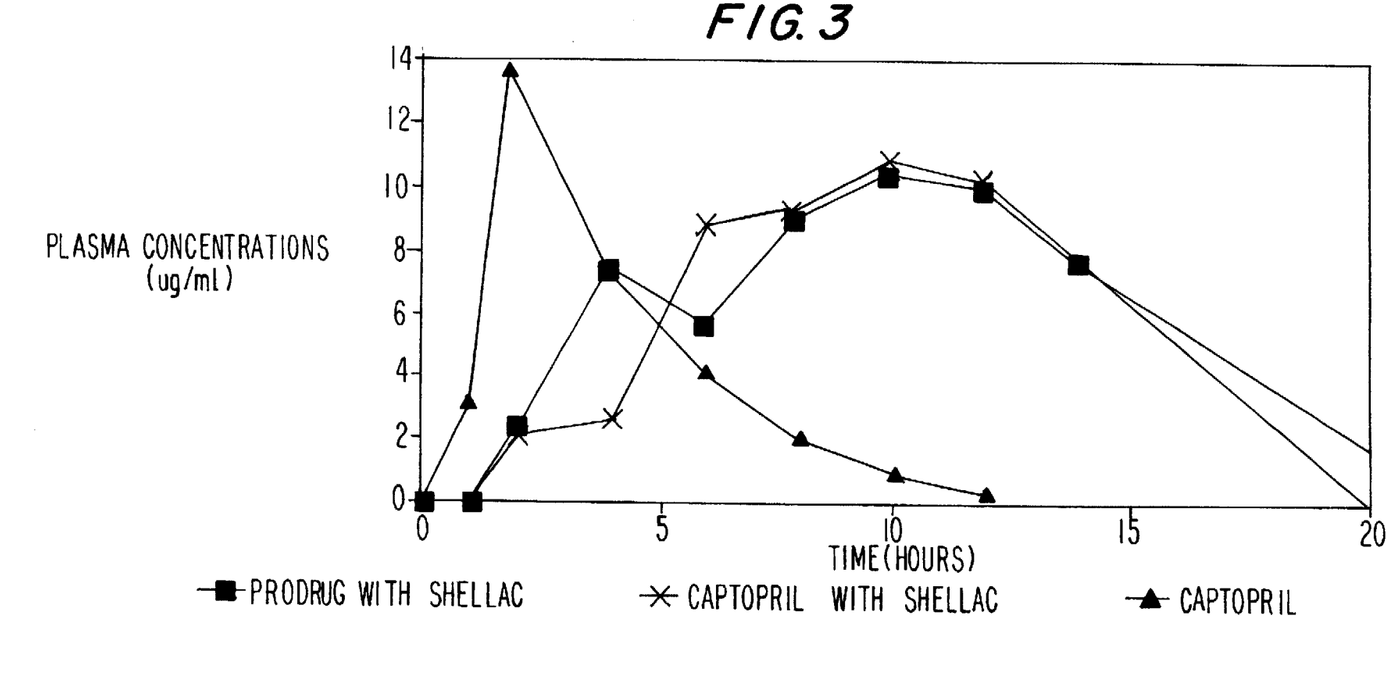
FIG. 3 is a graphical representation of the blood levels which were determined after oral administration to dogs of formulations of the invention.
Figure 4:
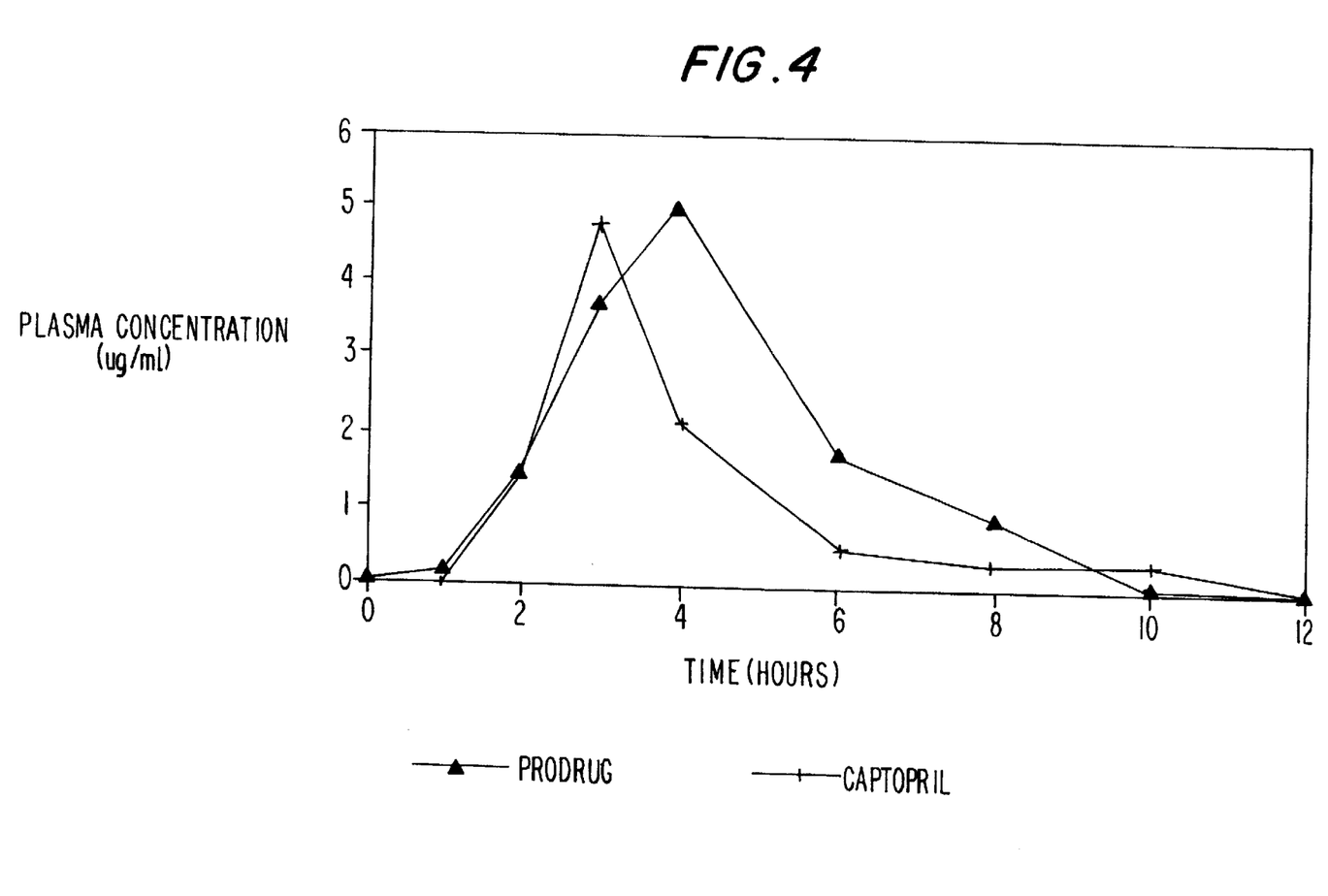
FIG. 4 is a graphical representation of the results of a comparative test of hydrogel formulations of captopril and a prodrug of captopril which were coated with cellulose acetate phthalate.

FIG. 2 shows the average of the results of the tests of the formulation of Example 1 (Prodrug SR) in 3 healthy human male volunteers; the formulation of Example 2 (Captopril SR) in 2 healthy human male volunteers; and the results of a control which was a captopril tablet without a hydrogel core or a coating which resists dissolution in the stomach. These tests show that the invention provides a dosage unit which provide blood levels of captopril which extend for 24 hours. FIG. 4 shows the results of a test of the formulation of Example 4 (Prodrug with shellac) in two male dogs and one female dog; a formulation of Example 4 (Captopril with shellac) in two male dogs and one female dog; and the results of a control of Example 4 in dogs. These tests show that the invention provides an extended level of activity in dogs which is at least 8 hours longer than the prior art dosage units of captopril.

We claim:

1. A controlled release pharmaceutical unit dose composition which comprises:

(a) an internal phase which comprises a pharmaceutically acceptable diluent and a prodrug of captopril of Formula I wherein R—COO— represents the acyloxy residue of captopril and $R_1$ and $R_2$ are the same or different and are selected from a group consisting of an alkyl group, an alkenyl group, an aryl group, an aralkyl group, a cycloalkyl group, in which the alkyl, alkenyl, aryl, aralkyl or cycloalkyl group is unsubstituted or substituted with one or more substituents selected from:

a halogen atom, a hydroxy group, a straight or branched-chain alkoxy group having the formula $R_3$—O—, wherein $R_3$ represents an alkyl group or any aryl group, which groups may be unsubstituted or substituted with one or more of a halogen atom or a hydroxy group, a carbamoyl group having the formula wherein $R_4$ and $R_3$ are the same or different and are hydrogen, an alkyl group or are selected from a group having the formula —$CH_2NR_7R_6$ wherein $R_6$ and $R_7$ are the same or different and are hydrogen, or an alkyl group; an amino group having the formula —$NR_8R_9$, wherein $R_8$ and $R_9$ are the same or different and are hydrogen, or an alkyl group; an acyloxy group having the formula —$COOR_{10}$, wherein $R_{10}$ is an alkyl, aryl or aralkyl group; an oxyacyl group having the formula $R_{11}COO$— wherein $R_{11}COO$— wherein $R_{11}$ is hydrogen, an alkyl group, an aryl group, an aralkyl group, a cycloalkyl group, in which the alkyl, aryl, aralkyl or cycloalkyl group is unsubstituted or substituted with one or more of a halogen atom, a hydroxy group, an alkoxy group of the formula $R_3$—O— as defined above, a carbamoyl group of the formula —$CONR_4R_5$ as defined above or an amino group having the formula —$NR_8R_9$ as defined above; and nontoxic pharmaceutically acceptable acid addition salts thereof; and (b) an external phase which comprises a coating which resists dissolution in the stomach.

2. A controlled release pharmaceutical unit dose composition which comprises:

(a) an internal phase which comprises a pharmaceutically acceptable diluent and a prodrug of captopril of Formula II:

; and (b) an external phase which comprises a coating which resists dissolution in the stomach.

3. A controlled release pharmaceutical unit dose composition which comprises:

(a) an internal phase which comprises a pharmaceutically acceptable diluent and a prodrug of captopril of Formula IV:

wherein $R_2$ is hydrogen or $R_5$—CO;

m is 1;

R is hydroxy, amino or lower alkoxy;

$R_1$ and $R_4$ each is hydrogen, lower alkyl or phenyl-lower alkyl;

$R_3$ is hydrogen, hydroxy or lower alkyl;

$R_5$ is lower alkyl, phenyl or phenyl-lower alkyl;

n is 0, 1 or 2 and basic salt thereof; and (b) an external phase which comprises a coating which resists dissolution in the stomach.

4. A controlled release pharmaceutical unit dose composition as defined in claim 1 wherein the internal phase contains an osmagent.

5. A controlled release pharmaceutical unit dose composition as defined in claim 4 wherein the internal phase contains fumaric acid and sodium chloride.

6. A controlled release pharmaceutical tablet for oral administration which comprises:

(a) an internal phase which comprises a prodrug of captopril in admixture with hydroxypropyl methyl cellulose and a pharmaceutical diluent; and (b) an external phase which comprises a coating which resists dissolution in the stomach but substantially dissolves in the intestines wherein the prodrug is of Formula I:

wherein R—COO— represents the acyloxy residue of captopril and $R_1$ and $R_2$ are the same or different and are selected from a group consisting of an alkyl group, an alkenyl group, an aryl group, an aralkyl group, a cycloalkyl group, in which the alkyl, alkenyl, aryl, aralkyl or cycloalkyl group is unsubstituted or substituted with one or more substituents selected from:

a halogen atom, a hydroxy group, a straight or branched-chain alkoxy group having the formula $R_3$—O—, wherein $R_3$ represents an alkyl group or any aryl group, which groups may be unsubstituted or substituted with one or more of a halogen atom or a hydroxy group, a carbamoyl group having the formula wherein $R_4$ and $R_3$ are the same or different and are hydrogen, an alkyl group or are selected from a group having the formula —$CH_2NR_7R_6$ wherein $R_6$ and $R_7$ are the same or different and are hydrogen, or an alkyl group; an amino group having the formula —$NR_8R_9$, wherein $R_8$ and $R_9$ are the same or different and are hydrogen, or an alkyl group; an acyloxy group having the formula —$COOR_{10}$, wherein $R_{10}$ is an alkyl, aryl or aralkyl group; an oxyacyl group having the formula $R_{11}COO$— wherein $R_{11}COO$— wherein $R_{11}$ is hydrogen, an alkyl group, an aryl group, an aralkyl group, a cycloalkyl group, in which the alkyl, aryl, aralkyl or cycloalkyl group is unsubstituted or substituted with one or more of a halogen atom, a hydroxy group, an alkoxy group of the formula $R_3$—O— as defined above, a carbamoyl group of the formula —$CONR_4R_5$ as defined above or an amino group having the formula —$NR_8R_9$ as defined above; and nontoxic pharmaceutically acceptable acid addition salts thereof.

7. A controlled release pharmaceutical tablet for oral administration which comprises:

(a) an internal phase which comprises a prodrug of captopril in admixture with hydroxypropyl methyl cellulose and a pharmaceutical diluent; and

(b) an external phase which comprises a coating which resists dissolution in the stomach but substantially dissolves in the intestines wherein the prodrug is of Formula II:

8. A controlled release pharmaceutical tablet for oral administration which comprises:

(a) an internal phase which comprises a prodrug of captopril in admixture with hydroxypropyl methyl cellulose and a pharmaceutical diluent; and (b) an external phase which comprises a coating which resists dissolution in the stomach but substantially dissolves in the intestines wherein the prodrug is of Formula III:

wherein $R_1$ is H or $R_3$ is a lower alkyl or phenyl $R_2$ is a lower alkyl or phenyl or and $R_4$, $R_5$ are H or a lower alkyl.

9. A controlled release pharmaceutical tablet for oral administration which comprises:

(a) an internal phase which comprises a prodrug of captopril in admixture with hydroxypropyl methyl cellulose and a pharmaceutical diluent; and (b) an external phase which comprises a coating which resists dissolution in the stomach but substantially dissolves in the intestines wherein the prodrug is of Formula IV:

wherein
R₂ is hydrogen or R₅—CO;
m is 2;
R is hydroxy, amino or lower alkoxy;
R₁ and R₄ each is hydrogen, lower alkyl or phenyl-lower alkyl;
R₃ is hydrogen, hydroxy or lower alkyl;
R₅ is lower alkyl, phenyl or phenyl-lower alkyl;
n is 0, 1 or 2 and basic salt thereof.

10. A controlled release pharmaceutical tablet for oral administration which comprises:

(a) an internal phase which comprises 10-25 wt % of captopril in admixture with 20-70 wt % of hydroxypropyl methyl cellulose and 15-35 wt % of lactose; and (b) an external phase which comprises a coating which comprises 7-10 wt % of shellac.

11. A compound of the formula:

* * * * *